(12) United States Patent
Amer et al.

(10) Patent No.: US 10,551,297 B2
(45) Date of Patent: Feb. 4, 2020

(54) THERMOGRAPHY IMAGE PROCESSING WITH NEURAL NETWORKS TO IDENTIFY CORROSION UNDER INSULATION (CUI)

(71) Applicant: Saudi Arabian Oil Company, Dhahran (SA)

(72) Inventors: Ayman Amer, Thuwal (SA); Ali Al Shehri, Thuwal (SA); Brian Parrott, Thuwal (SA); Muhammad Sarraj, Thuwal (SA)

(73) Assignee: Saudi Arabian Oil Company, Dhahran (SA)

( * ) Notice: Subject to any disclaimer, the term of this patent is extended or adjusted under 35 U.S.C. 154(b) by 340 days.

(21) Appl. No.: 15/712,490

(22) Filed: Sep. 22, 2017

(65) Prior Publication Data
US 2019/0094124 A1 Mar. 28, 2019

(51) Int. Cl.
*G01N 17/04* (2006.01)
*G06N 3/08* (2006.01)
(Continued)

(52) U.S. Cl.
CPC ............. *G01N 17/04* (2013.01); *G01K 1/045* (2013.01); *G01N 25/72* (2013.01); *G06N 3/0445* (2013.01);
(Continued)

(58) Field of Classification Search
CPC ........ G01N 17/04; G01N 25/72; G01N 27/90; G06N 3/08; G06N 3/0445; G06N 3/084; G06N 3/0454; G01K 1/045; G06F 16/285
See application file for complete search history.

(56) References Cited

U.S. PATENT DOCUMENTS

| 6,123,451 A * | 9/2000 | Schaefer ............... A22B 5/007 374/124 |
| 6,712,502 B2 | 3/2004 | Zalameda et al. |
(Continued)

FOREIGN PATENT DOCUMENTS

| WO | 2016183661 | 11/2016 |
| WO | 2017151757 | 9/2017 |

OTHER PUBLICATIONS

Usamentiaga et al., Infrared Thermography for Temperature Measurement and Non-Destructive Testing (Year: 2014).*
(Continued)

*Primary Examiner* — Mohammad K Islam
(74) *Attorney, Agent, or Firm* — Leason Ellis LLP

(57) ABSTRACT

A method for identifying corrosion under insulation (CUI) in a structure comprises receiving thermographs from the structure using an infrared camera, applying filters to the thermograph using a first machine learning system, initially determining a CUI classification based on output from the filters, and validating the initial CUI classification by an inspection of the structure. The first machine learning system is trained using results of the validation. Outputs of the first machine learning system and additional structural and environmental data are fed into a second machine learning system that incorporates information from earlier states into current states. The second machine learning system is trained to identify CUI according to changes in the outputs of the first machine learning system and the additional data over time until a second threshold for CUI classification accuracy is reached. CUI is thereafter identified using the first and second machine learning systems in coordination.

18 Claims, 5 Drawing Sheets

(51) Int. Cl.
*G06N 3/04* (2006.01)
*G01K 1/04* (2006.01)
*G01N 25/72* (2006.01)
G01N 27/90 (2006.01)
G06F 16/28 (2019.01)

(52) U.S. Cl.
CPC ............ *G06N 3/0454* (2013.01); *G06N 3/08* (2013.01); *G06N 3/084* (2013.01); *G01N 27/90* (2013.01); *G06F 16/285* (2019.01)

(56) References Cited

U.S. PATENT DOCUMENTS

| | | | |
|---|---|---|---|
| 8,596,861 | B2 | 12/2013 | Kane et al. |
| 2007/0217672 | A1 | 9/2007 | Shannon et al. |
| 2010/0100275 | A1* | 4/2010 | Mian ................... G01M 17/013 701/31.4 |
| 2010/0107767 | A1 | 5/2010 | Kane et al. |
| 2010/0266790 | A1* | 10/2010 | Kusinski ................... B32B 1/08 428/34.6 |
| 2016/0371316 | A1* | 12/2016 | Okanohara ............ G06N 7/005 |
| 2017/0030825 | A1* | 2/2017 | Goodwin ................ G01N 17/04 |
| 2017/0336156 | A1* | 11/2017 | Phillips ................... F28F 27/00 |
| 2018/0104742 | A1* | 4/2018 | Kottilingam .......... B29C 64/393 |
| 2018/0232870 | A1* | 8/2018 | Jo ............................ G06T 7/001 |
| 2018/0299392 | A1* | 10/2018 | Villette ...................... H04N 5/33 |
| 2018/0346737 | A1* | 12/2018 | Beele ....................... C09D 5/18 |
| 2019/0003983 | A1* | 1/2019 | Al-Omari .......... G01N 21/8851 |
| 2019/0079031 | A1* | 3/2019 | Safai ...................... G01N 23/02 |

OTHER PUBLICATIONS

Liu et al., CNN-based Automatic Coating Inspection System (Year: 2017).*
Fernandes et al., Artificial Neural Networks and Infrared Thermography for fiber orientation assessment (Year: 2017).*
Koštialová et al., Artificial Neural Networks Application in Thermography (Year: 2017).*
Lashkari et al., Full Intelligent Cancer Classification of Thermal Breast Images to Assist Physician in Clinical Diagnostic Applications (Year: 2015).*
Donahue, Jeff, et al., "Long-term recurrent convolutional networks for visual recognition and description," 2015 IEEE Conference on Computer Vision and Pattern Recognition (CVPR), IEEE, Jun. 7, 2015, pp. 2625-2634, XP032793708.
Hassan, M. et al., "Pipline Defect Classification by Using Non-Destructive Testing and Improved Support Vector Machine Classification," International Journal of Engineering and Innovative Technology (IJEIT), vol. 2, issue 7, pp. 85-93. Jan. 2013.

* cited by examiner

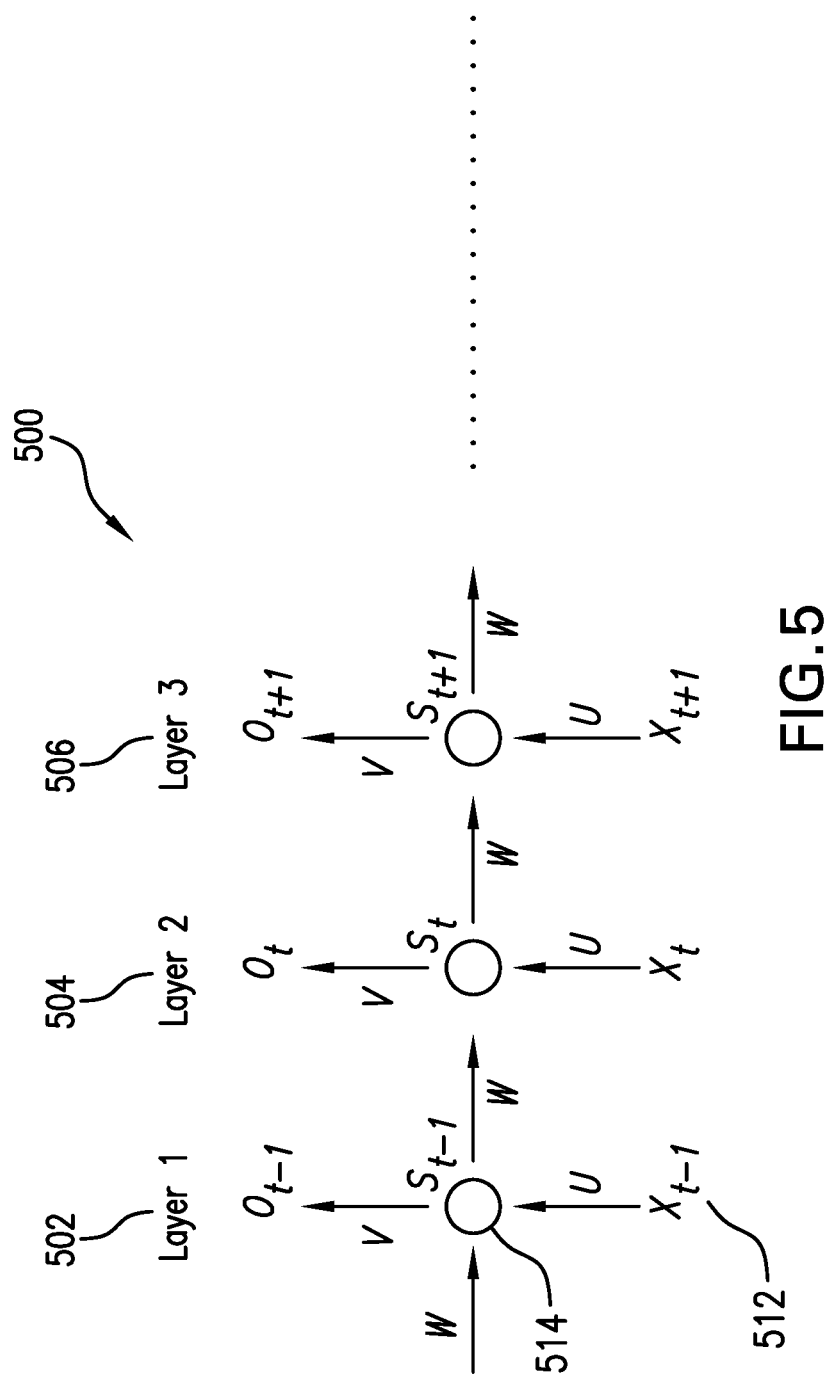

THERMOGRAPHY IMAGE PROCESSING WITH NEURAL NETWORKS TO IDENTIFY CORROSION UNDER INSULATION (CUI)

FIELD OF THE INVENTION

The present invention relates to inspection technologies, and in particular relates to a method and system in which thermography image processing is used with neural networks to identify corrosion under insulation (CUI).

BACKGROUND OF THE INVENTION

Corrosion under insulation (CUI) is a condition in which an insulated structure such as a metal pipe suffers corrosion on the metal surface beneath the insulation. As the corrosion cannot be easily observed due to the insulation covering, which typically surrounds the entire structure, CUI is challenging to detect. The typical causes of CUI are moisture buildup that infiltrates into the insulation material. Water can accumulate in the annular space between the insulation and the metal surface, causing surface corrosion. Sources of water that can induce corrosion include rain, water leaks, and condensation, cooling water tower drift, deluge systems and steam tracing leaks. While corrosion usually begins locally, it can progress at high rates if there are repetitive thermal cycles or contaminants in the water medium such as chloride or acid.

Studies indicate that 40 to 60% of pipe maintenance costs are caused by CUI. When CUI is undetected, the results of can lead to the shutdown of a process unit or an entire facility, and can lead to catastrophic incidents. Since it is a hidden corrosion mechanism, the damage remains unnoticed until insulation is removed or advanced NDT (non-destructive testing) techniques, such as infrared thermography, are used to ascertain the metal condition beneath the insulation. Removal of insulation can be a time-consuming and costly process, while the accuracy NDT techniques can be insufficient due to the large number of variables (e.g., geometrical, environmental, material-related), that cause false positives (incorrect detection of corrosion) and false negatives (incorrect non-detection of corrosion) in the detection process.

What is therefore needed is improvement in the NDT detection process that will enable external and confounding variables to be more properly accounted for so as to improve the accuracy of CUI detection.

SUMMARY OF THE INVENTION

Embodiments of the present invention provide a computer-implemented method for identifying corrosion under insulation (CUI) in a structure. The method comprises: a) receiving a thermograph captured from the structure using an infrared radiation sensor; b) applying one or more filters to the thermograph using a first machine learning system; c) initially determining a CUI classification based on output from the one or more filters; d) validating the initial CUI classification by an inspection of the structure; e) training the filters of the first machine learning system based on results of the validation; f) repeating steps a) through e) with additional thermograph data until a first threshold for CUI classification accuracy is reached. In further steps outputs of the first machine learning system and additional data related to the structure and environment conditions are input into a second machine learning system that incorporates information from earlier states into current states, and the second machine learning system is trained to identify CUI according to changes in the outputs of the first machine learning system and the additional data over time until a second threshold for CUI classification accuracy is reached. After the first and second thresholds are reached, CUI is identified in the structure based on current thermograph and additional data using the first and second machine learning systems in coordination.

In some embodiments, the first machine learning system includes a convolutional neural network. Implementations of the convolutional neural network can include a plurality of hierarchical layers, each hierarchical layer including a convolutional stage, a non-linear function stage and a pooling stage.

In some embodiments, the second machine learning system includes a recurrent neural network.

In some implementations, the additional data input to the second machine learning system includes ambient temperature, physical characteristics of the structure and weather conditions measured over time. Advantageously, the first and second machine learning systems can be trained to recognize false positive findings relative to reflection of infrared radiation from objects external from the structure.

Identification of CUI can include identifying vulnerable areas of the structure under the insulation that confine moisture with a high likelihood. In some implementations, validation is performed using at least two of the following techniques: pulsed eddy current evaluation, visual inspection, insulation removal and ultrasonic testing of wall thinning.

In further implementations, comprising preprocessing the thermograph data and the additional data to encode categorical variables and normalize continuous variables. Thermograph data, environmental variables, and structural information can be vectorized and used as inputs to the neural networks.

Embodiments of the present invention also provide a system for identifying corrosion under insulation (CUI) in a structure that comprises an infrared camera including a communication module that is positioned so as to capture infrared radiation emitted from the structure and adapted to communicate thermographs of the captured radiation via the communication module, and a computer system including a processor, memory and a communication module. The processor of the computer system is configured to execute a program that performs steps of: i) applying one or more filters to thermographs received from the infrared camera via the communication module, using a first machine learning system; ii) initially determining a CUI classification based on output from the one or more filters; iii) validating the initial CUI classification by an inspection of the structure; and iv) training the filters of the first machine learning system based on results of the validation. The processor is configured to repeat steps i) through iv) with additional thermograph data until a first threshold for CUI classification accuracy is reached. Outputs of the first machine learning system and additional data related to the structure and environment conditions are input into a second machine learning system that incorporates information from earlier states into current states. The second machine learning system is trained to identify CUI according to changes in the outputs of the first machine learning system and the additional data over time until a second threshold for CUI classification accuracy is reached. After the first and second thresholds are reached, CUI is identified in the structure based on current thermograph and additional data using the first and second machine learning systems in coordination.

Any combinations of the various embodiments and implementations disclosed herein can be used.

These and other aspects, features, and advantages can be appreciated from the following description of certain embodiments of the invention and the accompanying drawing figures and claims.

BRIEF DESCRIPTION OF THE DRAWINGS

FIG. 5 is a schematic illustration of an exemplary recurrent neural network (RNN) 500 that can be used in the context of the present invention.

It is noted that the drawings are illustrative and not necessarily to scale.

DETAILED DESCRIPTION CERTAIN OF EMBODIMENTS OF THE INVENTION

The embodiments disclosed herein relates to a system and method for the predictive detection of corrosion under insulation (CUI) considering all dependent and independent surrounding variables. The method includes capturing thermal image data (thermographs) of a structure using multiple IR (infrared) cameras over time, processing and analyzing the thermograph data to form an initial determination as to whether one or more anomalies are present in the structure that are indicative of corrosion, and performing subsequent inspection (validation) to assess the accuracy of the initial anomaly analysis. The results of the validation process are fed back in a supervised training process to improve the accuracy of anomaly analysis and classification over time. Additional evaluations can be done using electromagnetic NDT for the anomalies found by the thermography techniques to find correlative relationships and to increase the probability of CUI detection.

A principal purpose of the analysis and training is to enable the learning system to properly distinguish anomalies given the current environmental, structural and experimental parameters. A large number of parameters are accounted for in this process to prevent false positive and false negative determinations. As an example, detection of a hot spot on a structure while the structure is directly exposed to sunlight is not an anomalous condition. In contrast, if the hot spot occurs in the absence of sunlight and/or other external conditions that could be expected to cause the hot spot, an initial conclusion can be drawn that the insulation has been compromised in some way. In the latter case, the anomaly is recorded, and then after inspection, a report is generated to train the algorithm as to verify whether the recorded anomaly was an accurate identification of CUI. When done repeatedly, the verification and feedback causes the software to be more "intelligent" over time.

A number of different machine learning algorithms in different combinations can be used without limitation. One embodiment of a machine learning process that has proven particularly useful includes a combination of "convolutional" (CNN) and "recurrent" (RNN) neural networks. CNNs are particularly useful for stratifying thermal images into abstraction levels according to image topology, while RNNs are particularly useful for detecting patterns over time. Both factors are important, as the focus is on both detecting hotspots and on determining their development over time. In addition, in some embodiments, boosting algorithms, such as "Adaboost," can be used in conjunction with CNNs and RNNs in order to achieve higher accuracies at the expense of more computational time. Since mistakes are extremely costly, increasing accuracy at the sacrifice of computational time is an acceptable trade-off.

Figure 1:
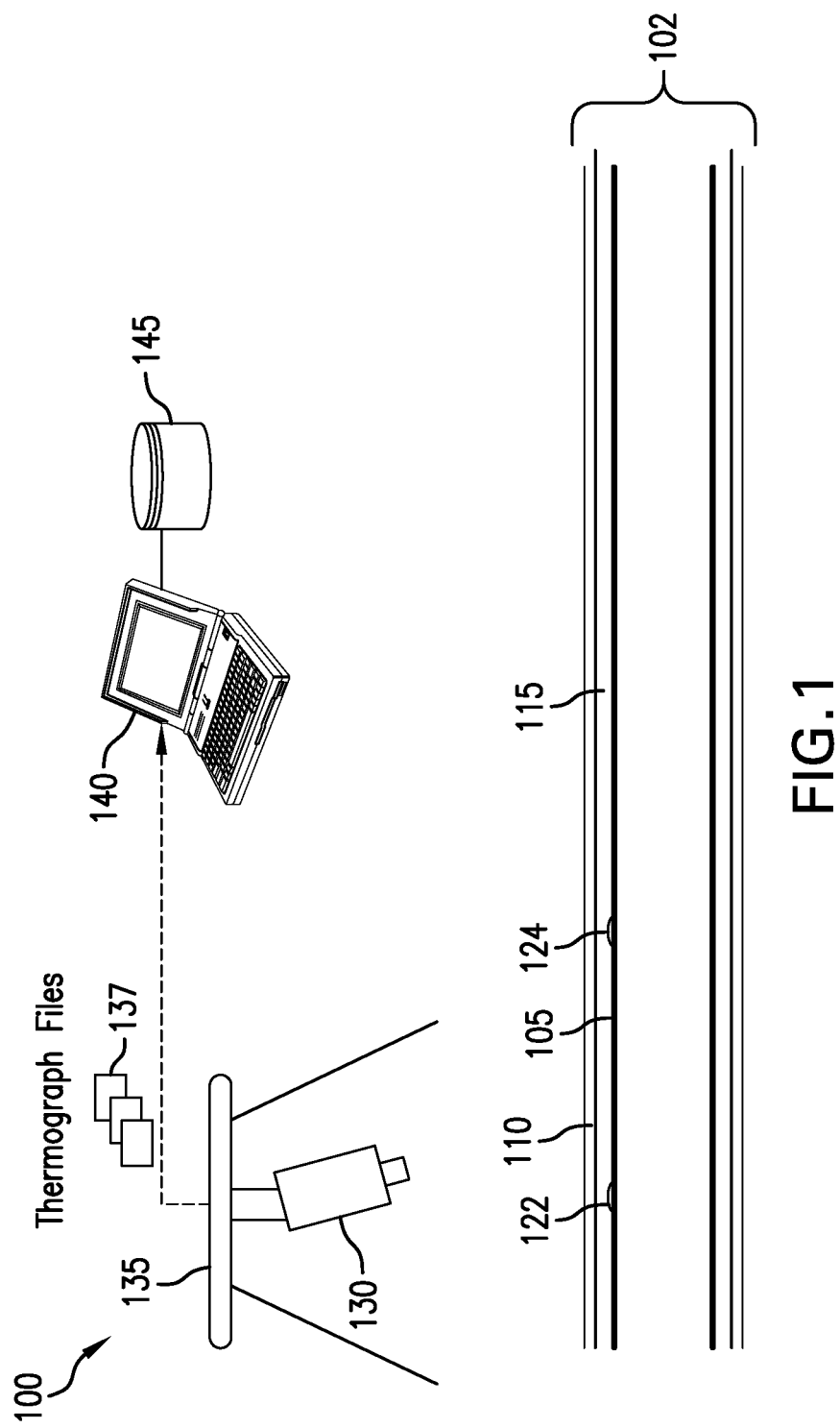
FIG. 1 is a schematic illustration of a system for detecting CUI using thermal imaging according to an embodiment of the present invention.

FIG. 1 is a schematic illustration of a system 100 for detecting CUI using thermal imaging according to an embodiment of the present invention. An exemplary structure 102 to be tested for CUI includes a pipe 105 that is surrounded by a layer of insulation 110. The insulation can comprise a foam layer with a thin metal wrap, or any other conventional structural insulation. There is an interface 115 positioned at the junction between the external surface of the pipe 105 and the insulation 110 in which water can accumulate and induce corrosion and degradation of the underlying pipe. In the illustration of FIG. 1, two areas where corrosion has built up on the pipe surface 122, 124 are shown.

In order to detect the corrosion beneath the insulation, an infrared camera 130 mounted on a movable platform 135 such as a tripod is positioned to take capture infrared radiation emitted from the structure 102 at various longitudinal positions and angles so as to capture data from the entire length and circumference of the structure. In alternate embodiments suited for structures in locations that are difficult to access, such as high-up pipe installations the infrared camera 130 can be mounted on an unmanned aerial vehicle (e.g., a drone). The unmanned aerial vehicle can be controlled remotely by inspection personnel to travel to structures of interest in such locations for gathering thermal image data. The platform 135 or UAV can include additional sensors for detecting environmental conditions including humidity, air pressure and wind speed. Thermal images, or thermographs, of the infrared radiation captured by the infrared camera 130 reveal temperature differentials and contrasts underneath the insulation that are undetectable in the visible spectrum radiation. More specifically, the IR thermal pattern on the surface of the pipeline is caused by heat conducted from the warm inner pipe through the insulation to an outer wrap.

The infrared camera 130 preferably captures thermographs representative of infrared radiation received from regions of the structure 103 continuously over a selected (long) duration. The camera 130 is adapted to convert the thermographs into a computer-readable file format (i.e., thermograph files 137 shown in FIG. 1). The thermograph files 135 are preferably communicated over a wireless communication mode (e.g., Bluetooth, Wi-Fi) to an onsite computer system 140 for further processing. In other implementations, the thermograph files 135 can be communicated over a wired connection, or alternatively, can be stored in a memory medium (e.g., SD card, flash drive) at the infrared camera and then manually transferred to the computer system 140.

Computer system 140 can be a tablet, laptop, smart phone or any other portable computing device capable of executing programs used for training a machine learning algorithm to detect CUI, as discussed in greater detail with respect to FIG. 2 below. Computer system is communicatively coupled to a database 145 that is used for storing the thermograph data on a long term basis. As many thermographs are taken at various locations on the structure and over extended periods of time (e.g., minutes up to several hours), the thermograph datasets can demand significant memory resources of the computer system 140 (e.g., in the gigabyte (GB) to terabyte (TB) range). Periodic archival from the computer system 140 to the database 145 can be performed to free up memory in the computer system 140.

In some implementations, it is preferable for inspection personnel to observe certain rules of thumb to achieve the best possible results. For example, it is preferable to perform IR inspections after sunset to prevent solar reflections from insulation covering. It is also preferable to account for, and minimize, thermal emissions and reflections from external sources, such as the ground.

Figure 2:
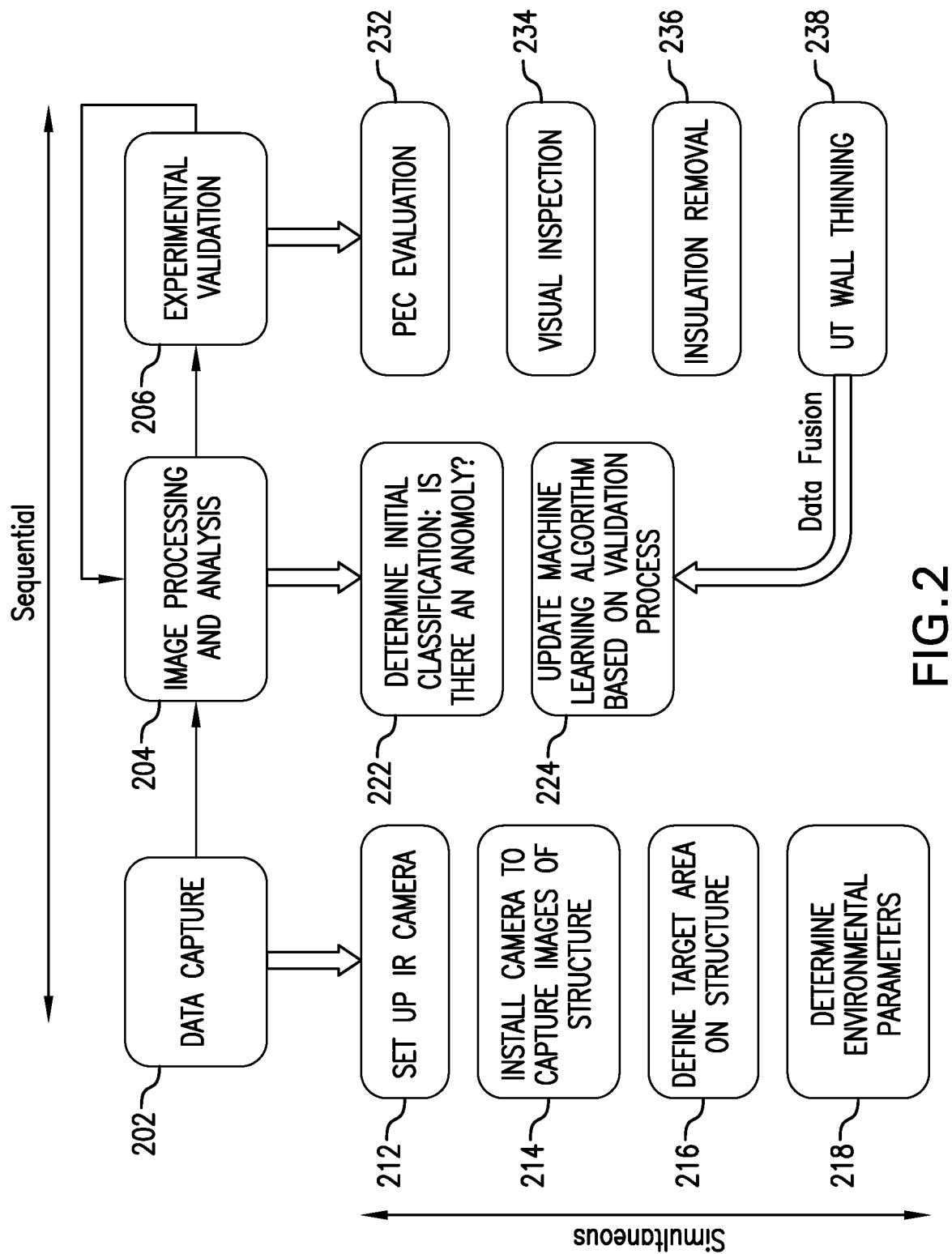
FIG. 2 is a schematic illustration of a method of thermal image processing with neural network for identification of CUI according to an embodiment of the present invention.

FIG. 2 is a schematic illustration of a method of thermal image processing with a neural network for identification of CUI according to an embodiment of the present invention. In terms of a high-level overview, the method includes three sequential stages: a data capture stage 202, followed by an image processing and analysis stage 204, which is followed by a validation stage 206. Information obtained by the validation stage 206 is fed back to the image processing and analysis stage 204. The data capture stage 202 encompasses setting up an apparatus to capture thermal image data from a structure of interest as well as determining environmental condition data. For example, the data capture stage 202 can involve setting up the infrared camera 212 to acquire images of a particular resolution for a selected duration, installing the IR camera 214 in the vicinity of the structure of interest or on a moving vehicle (e.g., a drone), defining a particular target area 216 on the structure for capturing of thermal images, and determining environmental parameters 218 such as humidity, air pressure, wind speed, etc.

The image processing and analysis phase 204 includes inputting the thermographs image data into a machine learning algorithm that classifies the images of the target area of the structure into various categories and enables an initial identification of whether the images show an anomalous condition 222 at the target area. An anomalous condition is an indication that CUI is possibly present in the target area of the structure. During a training process, the initial determination is not conclusive because the thermographs are being used as training data. In the subsequent validation process 206, a number of techniques can be used to establish whether the initial determination of the machine learning algorithm is correct. The various techniques can include pulsed eddy current evaluation 232, visual inspection 234, insulation removal 236, ultrasonic testing of wall thinning 238, any combination of these techniques and others without limitation, to form a definitive conclusion as to whether CUI is present in the target area of the structure. Thus, during the learning process, either destructive or non-destructive techniques can be used to validate whether CUI is present.

Discrepancies between the initial identification and the validation are fed back into the machine learning algorithm 224 to update the activations (the weights used for the various input parameters of the thermographs and environmental data) with the aim of optimizing the algorithm according to the techniques of a supervised learning process. Once the accuracy of the machine learning algorithm has improved to a sufficient level, validation is no longer performed and the image processing and analysis stage 204 is used to detect and identify CUI directly. The image processing and analysis stage can employ any one or more of a variety of supervised machine learning algorithms and techniques including, without limitation, convolutional neural networks, recurrent neural networks, ensemble learning and boosting methods such as Adaboost, decision trees, and support vector machines.

In one advantageous embodiment, a convolutional neural network (CNN) is used to hierarchically classify the captured thermograph data. This is followed by processing thermograph data captured over a significant duration of time using a recurrent neural network (CNN). In some implementations, a boosting algorithm can be used in conjunction with the CNN and RNN in order to achieve higher accuracies. While the boosting algorithm increases the overall number of computations, and thus increases computational time, additional accuracy is a more significant factor due to the high cost of misidentification.

In some embodiments of the present invention, a preprocessing phase is performed. In the preprocessing phase, inputs to the neural network algorithms, including thermograph and environmental data, are encoded and/or normalized. Variables that are categorical (i.e., that are limited to a small number of possible discrete values) can be one-hot-encoded before being fed to the neural network. Alternatively, variables that are continuous (i.e., can have a large number of possible values) are normalized, and the means of the continuous variables are shifted to zero before being fed into the neural network.

The output of the preprocessing phase is an amalgamation of all of the inputs. The amalgamation can be achieved using various techniques (or combinations thereof) including, for example: a) concatenating variables to each other (e.g., appending environmental variables to thermographs—as if they are an extended part of the images); b) flattening each of the inputs into an n-dimensional vector and then concatenating the n-dimensional vectors into a single long vector; and/or c) applying an encoder, which can be implemented using an additional network, to compress or reduce all of the inputs into a single input before feeding it into the main network. All input variables, including thermographs data, environmental, or other variables, undergo the same preprocessing procedure. The CNN operates to emphasize and highlight relevant variables relative to less relevant variables.

Figure 3:
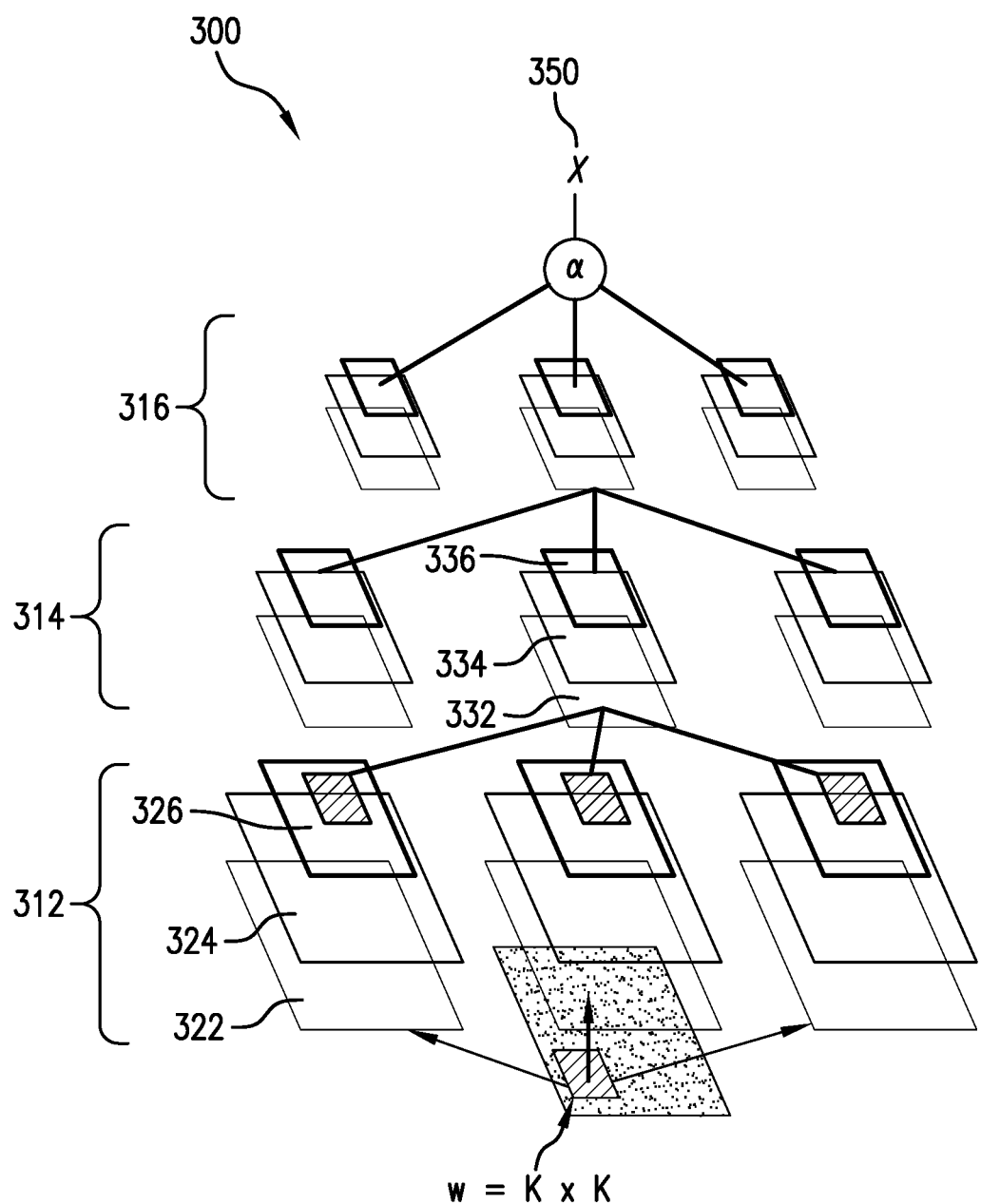
FIG. 3 is a schematic illustration of an exemplary convolutional neural network that can be used in the context of the present invention.
Figure 4:
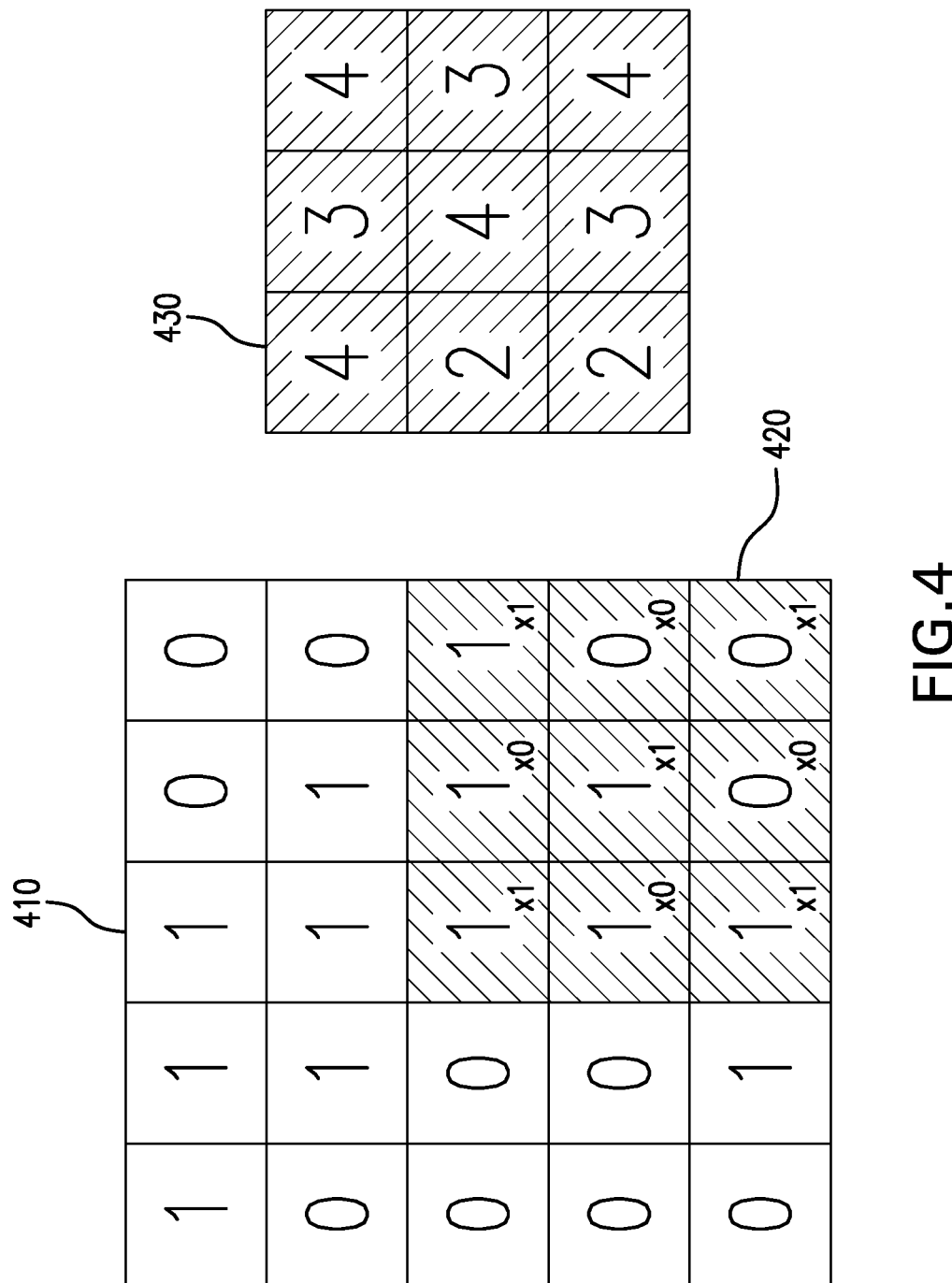
FIG. 4 is a schematic illustration showing an example of how convolution can be applied to image data.

A schematic illustration of an exemplary convolutional neural network (CNN) 300 that can be used in the context of the present invention is shown in FIG. 3. In the example shown, CNN 300 receives as input a localized section of an image 302. As shown, CNN 300 includes three hierarchical levels 312, 314, 316. It is noted that fewer or a larger number of hierarchical levels can be used. The first hierarchical level 312 includes three parallel processing paths, each processing path in turn including three distinct processing stages. This complex scheme can be clarified by explanation of the stages of a single processing path at a single level. Referring now to the leftmost path at the first hierarchical level, a first convolutional stage 322 applies a first convolution function (filter) to the input image data. It is noted that the other processing paths operate on another localized section of the input image. Each hierarchical level can apply a different convolution function to the data it receives to better identify features in the image. The filters can, for example, blur contrasts between neighboring image values by averaging, or, conversely, some filters can enhance differences to clarify edges. Each filter composes a local patch of lower-level features into higher-level representation. In this manner, edges can be discerned from pixels, shapes from can be discerned from edges, and so on. An example of how convolution can be applied to image data is shown in FIG. 4. In FIG. 4, a 5×5 square sample of pixel values 410 is shown to which a convolution matrix 420, or 'window' can be applied by sliding the convolution matrix 420 over the values of the sample values 410. In the example shown, the convolution matrix is a 3×3 matrix function that multiplies all values along the diagonals by one and values not along the diagonals by zero. The sum of each 3×3 section of the image sample as acted upon by the convolution matrix is provided to an output matrix 430. The output matrix 430 is then fed as output to the next stage of the hierarchical layer.

The next stage of hierarchical layer 312 applies a non-linear function 324 to the data of the convolutional stage, such as a ReLU (rectified linear unit) or tanh function. This stage can be represented as $y_{i,j}=f(a_{i,j})$, in which f represents the non-linear function and $a_{i,j}$ represents is a pixel of the ith row and jth column from the output matrix of the convolution stage. The output of the non-linear function stage 324 is thus a modified version of the matrix output from convolutional stage 322. The final stage of hierarchical level 312 is a pooling stage 326 that can be used to simplify the data. For example, the pooling stage can apply a maximum function to output only the maximum value of the non-linear function of a number of rows and columns of pixels of the output matrix from the non-linear stage. After simplifying the data, the outputs of the pooling stages of all of the three processing paths can be summed and then input to the convolution stage 332 of one of the processing paths of the next hierarchical layer 314. In hierarchical layer 314, similar or different convolution matrices can be used to process the data received from the first hierarchical layer 312, and the same or different non-linear functions and simplification functions can be used in the following non-linear stage 334 and pooling stage 336. Output from the parallel processing paths of the second hierarchical layer 314 can be similarly pooled and then provided as an output matrix to the third hierarchical layer 316, in which further processing takes place. The final output 350 can be interpreted as a class label probability, or put another way, the most likely classification for the image. Classifications can include different types of hot spots indicative of temperature differentials and possible CUI.

The CNN learns by validation and backward propagation. This is equivalent to setting values of the output 350 and then running the algorithm backwards from the higher hierarchical layers to the lower layers and modifying the convolution matrices to yield better results using an optimization function. After training, the CNN should be able to accurately classify an input thermograph into one of the preset categories such as a hot spot, non-hot spot, etc.

While the CNN is an efficient and useful methodology for stratifying input images into abstraction levels according to the thermograph image topology, it is not best suited for detecting patterns over time. Embodiments of the present invention therefore employ a recurrent neural network (RNN) in association with the CNN to improve time-based pattern recognition.

FIG. 5 is a schematic illustration of an exemplary recurrent neural network (RNN) 500 that can be used in the context of the present invention. The RNN 500 includes a number of layers of which three layers 502, 504, 506 are explicitly shown. The RNN is best explained with reference to the second layer 504. In this layer, $x_t$ is the input to the layer at time step t. The input $x_t$ 512 can be a vector or matrix of values. $S_t$ 514 represents the hidden state at time step t. The hidden state can be considered as the "memory" of the RNN. The hidden state is calculated based on the previous hidden state and the input at the current step: $s_t=f(Ux_t+Ws_{t-1})$. The function f is a typically a nonlinear function such as tanh or ReLU. The first hidden state is typically initialized to all zeroes. $S_t$ is modified by parameter vector V to yield $O_t$, which is the output at step t. $O_t$ can be interpreted as a matrix or vector of probabilities for the next state s+1. The RNN 500 shares the same parameters (U, V, W above) across all steps. This reflects the fact that the same task at each step is performed at each step but with different inputs. This reduces the total number of parameters to learn, and thus also reduces processing time. While in the example shown, each layer has outputs at each time step, this is not necessary as in some implementation only the final output is of interest.

The RNN can be used to detect changes to thermographs over time, and to account for environmental variables. These variables can be introduced as parameters into the RNN along with thermograph data. The most important variables to consider can be split into four main categories: i) ambient conditions, ii) conditions of the structure of interest, iii) conditions of any CUI identified and iv) configuration of the IR camera with respect to the structure. For example, ambient conditions to account for in the analysis include, without limitation, the ambient temperature over time, fluid temperature within the structure, weather conditions including precipitation, dust, and wind speed, the time of year, and the amount of sunlight exposure in the location. The conditions of the structure include, without limitation, the dimensions of the structure and insulation, the insulation type and physical properties, arrangements of joints, elbows, dead-legs, etc., and optical characteristics of the exposed surface, reflectivity of the structural metal, and any observed defects (e.g., voids in the insulation). The conditions of any CUI identified include, without limitation, the location (up or down) and growth direction of the CUI, and how the CUI is distributed with respect to unimpaired areas. The main factor of the configuration of the IR camera is the distance between the IR camera and the structure.

Using the information of the tendency of the various thermographs and conditions over time, further levels of analysis can be conducted. For example, the analysis can focus on: how the temperature difference data (e.g., hot spots, anomalies) at various locations on the structure are related or distinguishable; the overall tendency of the temperature and anomalies over time; whether the features that change over time appear, disappear or degrade; whether effects are more probably due to extraneous emissivity and reflections rather than CUI conditions.

In some embodiments, a boosting algorithm, such as Adaboost, can be used in conjunction with CNNs and RNNs in order to achieve higher accuracies at the expense of additional computation. Boosting is typically used for combining and improving "weak learners", which are machine learning algorithms that, even after training, have a high error rate identification, into a "strong" learner. Adaboost combines the output of the weak learning algorithms into a weighted sum that represents the final output of the boosted classifier. The weight of any given algorithm is based on the accuracy of that algorithm. While CNNs and RNNs can generally be trained to be strong learners, it can be advantageous to add boosting to further ensure accuracy because mistakes can be extremely costly. Increasing accuracy at the sacrifice of computational time can be an acceptable trade-off. In addition, boosting can be useful in the designing phase for testing CNNs and RNNs.

The present invention provides a number of advantages that enable accurate detection of CUI. Water and moisture spots can normally dry easily without being detected on time. However, by continuously monitoring via IR imaging, it is possible to capture and identify vulnerable locations that confine water and moisture spots. The methods of the present invention enable budgeting of annual inspection plan that can be implemented according to the monitoring outcomes and image processing results. The monitoring methods also are intrinsically safe and the automation of the method eliminates manual inspection errors. As long as the temperature in the pipe is sufficiently different than the ambient temperature, the IR evaluation method generally performs up to required standards. Anomalies found by IR can be evaluated further using other techniques (e.g., pulsed eddy current (PEC)) using a correlative approach. Additionally, IR imaging can be used in cold-weather applications to detect insulation failures and icing.

It is to be understood that any structural and functional details disclosed herein are not to be interpreted as limiting the systems and methods, but rather are provided as a representative embodiment and/or arrangement for teaching one skilled in the art one or more ways to implement the methods.

The methods described herein may be performed by software in machine readable form on a tangible storage medium e.g. in the form of a computer program comprising computer program code means adapted to perform all the steps of any of the methods described herein when the program is run on a computer and where the computer program may be embodied on a computer readable medium. Examples of tangible storage media include computer storage devices comprising computer-readable media such as disks, thumb drives, memory etc. and do not include propagated signals. Propagated signals may be present in a tangible storage media, but propagated signals per se are not examples of tangible storage media. The software can be suitable for execution on a parallel processor or a serial processor such that the method steps may be carried out in any suitable order, or simultaneously.

It is to be further understood that like numerals in the drawings represent like elements through the several figures, and that not all components and/or steps described and illustrated with reference to the figures are required for all embodiments or arrangements The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Terms of orientation are used herein merely for purposes of convention and referencing, and are not to be construed as limiting. However, it is recognized these terms could be used with reference to a viewer. Accordingly, no limitations are implied or to be inferred.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A computer-implemented method for identifying corrosion under insulation (CUI) in a structure, comprising:
    a) receiving a thermograph captured from the structure using an infrared radiation sensor and additional data related to the structure and environmental conditions;
    b) applying one or more filters to the thermograph and the additional data using a first machine learning system;
    c) initially determining a CUI classification based on output from the one or more filters;
    d) validating the initial CUI classification by an inspection of the structure;
    e) training the filters of the first machine learning system based on results of the validation;
    f) repeating steps a) through e) with additional thermograph data until a first threshold for CUI classification accuracy is reached;
    g) inputting outputs of the first machine learning system and additional data related to the structure and environment conditions into a second machine learning system that incorporates information from earlier states into current states;
    h) training the second machine learning system to identify CUI according to changes in the outputs of the first machine learning system and the additional data over time until a second threshold for CUI classification accuracy is reached; and
    i) after the first and second thresholds are reached, identifying CUI in the structure based on current thermograph and additional data using the first and second machine learning systems in coordination.

2. The computer-implemented method of claim 1, wherein the first machine learning system includes a convolutional neural network.

3. The computer-implemented method of claim 2, wherein the convolutional neural network includes a plurality of hierarchical layers, each hierarchical layer including a convolutional stage, a non-linear function stage and a pooling stage.

4. The computer-implemented method of claim 2, wherein the second machine learning system includes a recurrent neural network.

5. The computer-implemented method of claim 4, wherein the additional data includes ambient temperature, physical characteristics of the structure and weather conditions measured over time.

6. The computer-implemented method of claim 5, wherein the first and second machine learning systems are trained to recognize false positive findings relative to reflection of infrared radiation from objects external from the structure.

7. The computer-implemented method of claim 1, wherein identification of CUI includes identifying vulnerable areas of the structure under the insulation that confine moisture with a high likelihood.

8. The computer-implemented method of claim 1, wherein validation is performed using at least two of pulsed eddy current evaluation, visual inspection, insulation removal and ultrasonic testing of wall thinning.

9. The computer-implemented method of claim 1, further comprising preprocessing the thermograph data and the additional data to encode categorical variables and normalize continuous variables.

10. A system for identifying corrosion under insulation (CUI) in a structure, comprising:

An infrared camera including a communication module, the infrared camera positioned so as to capture infrared radiation emitted from the structure and adapted to communicate thermographs of the captured radiation via the communication module;

a computer system including a processor, memory and a communication module, the processor being configured to execute a program that performs steps of:

i) applying one or more filters to thermographs received from the infrared camera via the communication module and additional data related to the structure and environmental conditions, using a first machine learning system;

ii) initially determining a CUI classification based on output from the one or more filters;

iii) validating the initial CUI classification by an inspection of the structure;

iv) training the filters of the first machine learning system based on results of the validation;

v) repeating steps i) through iv) with additional thermograph data until a first threshold for CUI classification accuracy is reached;

vi) inputting outputs of the first machine learning system and additional data related to the structure and environment conditions into a second machine learning system that incorporates information from earlier states into current states;

vii) training the second machine learning system to identify CUI according to changes in the outputs of the first machine learning system and the additional data over time until a second threshold for CUI classification accuracy is reached; and after the first and second thresholds are reached, identifying CUI in the structure based on current thermograph and additional data using the first and second machine learning systems in coordination.

11. The system of claim 10, wherein the first machine learning system includes a convolutional neural network.

12. The system of claim 11, wherein the convolutional neural network includes a plurality of hierarchical layers, each hierarchical layer including a convolutional stage, a non-linear function stage and a pooling stage.

13. The system of claim 11, wherein the second machine learning system includes a recurrent neural network.

14. The system of claim 13, wherein the additional data includes ambient temperature, physical characteristics of the structure and weather conditions measured over time.

15. The system of claim 14, wherein the first and second machine learning systems are trained to recognize false positive findings relative to reflection of infrared radiation from objects external from the structure.

16. The system of claim 10, wherein identification of CUI includes identifying vulnerable areas of the structure under the insulation that confine moisture with a high likelihood.

17. The system of claim 10, wherein validation is performed using at least two of pulsed eddy current evaluation, visual inspection, insulation removal and ultrasonic testing of wall thinning.

18. The system of claim 10, wherein the computer system preprocesses the thermograph data and the additional data to encode categorical variables and normalize continuous variables.

* * * * *